United States Patent
Bergin et al.

(10) Patent No.: US 7,622,628 B2
(45) Date of Patent: Nov. 24, 2009

(54) HEMOSTATIC WIRE GUIDED BANDAGE AND METHOD OF USE

(75) Inventors: Patrick J. Bergin, Eugene, OR (US); Jeffrey P. Wensel, Eugene, OR (US)

(73) Assignee: Innovasa Corporation, Eugene, OR (US)

( * ) Notice: Subject to any disclaimer, the term of this patent is extended or adjusted under 35 U.S.C. 154(b) by 0 days.

(21) Appl. No.: 11/332,784

(22) Filed: Jan. 12, 2006

(65) Prior Publication Data
US 2006/0276837 A1 Dec. 7, 2006

Related U.S. Application Data

(63) Continuation-in-part of application No. 11/245,956, filed on Oct. 7, 2005, now abandoned.

(60) Provisional application No. 60/688,510, filed on Jun. 7, 2005, provisional application No. 60/693,706, filed on Jun. 24, 2005, provisional application No. 60/677,863, filed on May 4, 2005, provisional application No. 60/723,878, filed on Oct. 5, 2005.

(51) Int. Cl.
A61F 13/00 (2006.01)
A61F 11/00 (2006.01)
A61M 37/00 (2006.01)

(52) U.S. Cl. ............... 602/42; 604/164.04; 604/174; 604/288.01; 604/304; 606/108; 606/213; 606/232

(58) Field of Classification Search ............ 606/213, 606/108, 187, 186, 95, 232; 604/174–175, 604/180, 288.01, 288.02, 288.03, 164.04, 604/228.02, 228.04, 289, 150, 304–308, 604/890; 602/47, 41, 48, 42, 43, 46, 49, 602/50, 52–54, 58
See application file for complete search history.

(56) References Cited

U.S. PATENT DOCUMENTS 3,927,669 A * 12/1975 Glatt .................... 602/47

(Continued)

FOREIGN PATENT DOCUMENTS

WO WO 92/22252 12/1992
WO WO 00/033744 6/2000

OTHER PUBLICATIONS

Abbott Vascular Devices, *Starclose Vascular Closure System*, printed Oct. 31, 2006, 4 pages, Abbott Park, IL., USA.
Argentum Medical LLC, *SilverlonB Contact Wound Dressings*, Jan. 24, 2003, 5 pages.
Argentum Research, *Silver-nylon wound packing strips*, Sep. 24, 1999, 6 pages.
Cath Lab Digest, Products, Current/Archives issues, printed Sep. 28, 2006, 22 pages.
Datascope Intervascular, *Products / Procedures*, printed Sep. 28, 2006, 12 pages.
FDA Regulations, *Plastic Surgery Database, Catheters*, printed Sep. 28, 2006, 6 pages.

(Continued)

*Primary Examiner*—Tatyana Zalukaeva
*Assistant Examiner*—Keri J Nicholson
(74) *Attorney, Agent, or Firm*—Finnegan, Henderson, Farabow, Garrett & Dunner, LLP

(57) ABSTRACT

Some embodiments of the invention provide an apparatus for achieving hemostasis in a puncture tract that is created during a medical procedure. The puncture typically extends from the epidermis to the vasculature in a living organism. In some embodiments, the apparatus includes (1) a plug for subcutaneous placement within the puncture tract, and (2) a delivery mechanism for delivering and maintaining the plug within the puncture tract until hemostasis is achieved. The apparatus also includes in some embodiments a lubricious sheath that is placed around the plug to facilitate the insertion of the plug into the puncture tract.

52 Claims, 9 Drawing Sheets

U.S. PATENT DOCUMENTS

| | | | |
|---|---|---|---|
| 4,826,487 A * | 5/1989 | Winter | 604/175 |
| 4,863,438 A * | 9/1989 | Gauderer et al. | 604/247 |
| 4,890,612 A | 1/1990 | Kensey | |
| 5,021,059 A | 6/1991 | Kensey et al. | |
| 5,061,274 A | 10/1991 | Kensey | |
| 5,108,421 A | 4/1992 | Fowler | |
| 5,192,302 A | 3/1993 | Kensey et al. | |
| 5,221,259 A | 6/1993 | Weldon et al. | |
| 5,222,974 A | 6/1993 | Kensey et al. | |
| 5,242,415 A * | 9/1993 | Kantrowitz et al. | 604/175 |
| 5,263,922 A * | 11/1993 | Sova et al. | 602/59 |
| 5,292,332 A | 3/1994 | Lee | |
| 5,320,639 A | 6/1994 | Rudnick | |
| 5,383,896 A | 1/1995 | Gershony et al. | |
| RE34,866 E | 2/1995 | Kensey et al. | |
| 5,437,631 A | 8/1995 | Janzen | |
| 5,443,481 A | 8/1995 | Lee | |
| 5,507,721 A | 4/1996 | Shippert | |
| 5,540,715 A | 7/1996 | Katsaros et al. | |
| 5,545,178 A * | 8/1996 | Kensey et al. | 606/213 |
| 5,569,207 A * | 10/1996 | Gisselberg et al. | 604/175 |
| 5,571,181 A * | 11/1996 | Li | 623/23.75 |
| 5,613,974 A | 3/1997 | Andreas et al. | |
| 5,649,959 A | 7/1997 | Hannam et al. | |
| 5,782,861 A | 7/1998 | Cragg et al. | |
| 5,810,846 A | 9/1998 | Virnich et al. | |
| 5,873,890 A | 2/1999 | Porat | |
| 6,007,563 A | 12/1999 | Nash et al. | |
| 6,120,524 A | 9/2000 | Taheri | |
| 6,206,893 B1 | 3/2001 | Klein et al. | |
| 6,261,258 B1 | 7/2001 | Saines | |
| 6,296,657 B1 * | 10/2001 | Brucker | 606/213 |
| 6,325,789 B1 | 12/2001 | Janzen et al. | |
| 6,368,341 B1 | 4/2002 | Abrahamson | |
| 6,383,208 B1 | 5/2002 | Sancoff et al. | |
| 6,482,179 B1 | 11/2002 | Chu et al. | |
| 6,524,321 B2 | 2/2003 | Kanesaka | |
| 6,554,851 B1 | 4/2003 | Palasis et al. | |
| 6,623,509 B2 | 9/2003 | Ginn | |
| 6,626,918 B1 | 9/2003 | Ginn et al. | |
| 6,663,655 B2 | 12/2003 | Ginn et al. | |
| 6,679,904 B2 | 1/2004 | Gleeson et al. | |
| 6,682,489 B2 | 1/2004 | Tenerz et al. | |
| 6,743,195 B2 | 6/2004 | Zucker | |
| 6,780,197 B2 | 8/2004 | Roe et al. | |
| 6,787,682 B2 | 9/2004 | Gilman | |
| 6,846,319 B2 | 1/2005 | Ginn et al. | |
| 6,890,342 B2 | 5/2005 | Zhu et al. | |
| 2002/0072768 A1 | 6/2002 | Ginn | |
| 2002/0077604 A1 | 6/2002 | Willis et al. | |
| 2003/0023267 A1* | 1/2003 | Ginn | 606/213 |
| 2003/0073979 A1 | 4/2003 | Naimark et al. | |
| 2003/0093017 A1 | 5/2003 | Loud | |
| 2003/0093075 A1 | 5/2003 | Levinson | |
| 2003/0125766 A1* | 7/2003 | Ding | 606/213 |
| 2003/0139696 A1 | 7/2003 | Boukanov et al. | |
| 2003/0195560 A1* | 10/2003 | Ginn | 606/213 |
| 2003/0233120 A1* | 12/2003 | Akerfeldt | 606/213 |
| 2005/0113761 A1* | 5/2005 | Faust et al. | 604/180 |
| 2006/0276836 A1 | 12/2006 | Bergin et al. | |
| 2006/0276838 A1 | 12/2006 | Wensel et al. | |
| 2008/0015481 A1 | 1/2008 | Bergin et al. | |

OTHER PUBLICATIONS

Fibres & Textiles in Eastern Europe, "Chitosan Medical Dressings", vol. 13, No. 6 (54), Dec. 2005, 3 pages.
Massat, Mary B., *Vascular Closure Devices*, Jan./Feb. 2003, 5 pages.
Medafor, Inc, *Summary of effectiveness: Dressing*, Dec. 17, 2003, 6 pages.
On Site Gas Systems, Inc, *Summary of effectiveness: Traumatic Wound Dressing*, May 2002, 6 pages, Newington, CT., USA.
PR Newswire. *Abbott Submits StarClose(TM) Vascular Closure System for FDA Approval*, printed Sep. 28, 2006, 3 pages.
SUB-Q, Inc., *Premarket Approval Application: QuickSeal Femoral Arterial Closure System Summary of Safely and Effectiveness Data*, printed Sep. 28, 2006, 16 pages.
Vascular Solutions, *Products*, printed Sep. 28, 2006, 19 pages, Minneapolis, MN., USA.
"Cardiac Imaging," *Cath Lab Digest*, http://www.cathlabdigest.com/cardiac-imaging, Sep. 28, 2006, pp. 1-2.
"Cath Lab Digest —ISSN: 1073-2667—vol. 14,—Issue 6 (Jun. 2006)—Jun. 2006," *Cath Lab Digest*, Jun. 2006, pp. 1-3.
"Current Issue," *Cath Lab Digest*, Sep. 2006, pp. 1-3.
"HMP Communications Webcasts & Symposia," *Cath Lab Digest*, http://www.cathlabdigest.com/webcasts.cfm, Sep. 28, 2006, pp. 1-2.
"Stents," *Cath Lab Digest*, http://www.cathlabdigest.com/stents, Sep. 28, 2006, pp. 1-2.
"Summary of Safety and Effectiveness Data; QuickSeal™ Femoral Arterial Closure System; Premarket Approval Application No. P010049," *Center for Devices and Radiological Health*, http://www.fda.gov/cdrh/pdf/P010049b.pdf, Mar. 25, 2002, pp. 1-16.
"Title 21—Food and Drugs," *FDA CFR Title 21 Database*, Jan. 14, 2000, pp. 1-6.
"Vessel Closure," *Cath Lab Digest*, http://www.cathlabdigest.com/vessel-closure, Sep. 28, 2006, pp. 1-2.
Abbott Vascular Devices, "Advancing vascular care. Together.", http://www.abbottvascularcom/, Oct. 31, 2006, pp. 1-2.
Datascope, "Datascope Intervascular," http://www.intervascularcom/, Sep. 28, 2006, p. 1.
Datascope, "Cardiac Assist," http://www.datascope.com/ca/cardiacassist.html, Sep. 28, 2006, pp. 1-2.
Datascope, "Interventional Products," http://www.datascope.com/ip/index.html, Sep. 28, 2006, pp. 1-2.
Datascope, "Patient Monitoring," http://www.datascope.com/pm/patientmonitoring.html, Sep. 28, 2006, pp. 1-2.
Datascope, "Products," http://www.datascope.com/pr/products.html, Sep. 28, 2006, p. 1.
Datascope, "VasoSeal ES™ Overview," http://www.datascope.com/ip/esoverview.html, Sep. 28, 2006, p. 1.
Datascope, "VasoSeal ES™ Procedure," http://www.datascope.com/ip/esprocedure.html, Sep. 28, 2006, pp. 1-3.
DRG® MEDTEK, "StarClose Vascular Closure System," http://www.drg.alpha.pl/starclose.html, Oct. 31, 2006, pp. 1-2.
Elkin, Doug, "Abbott Submits StarClose(TM) Vascular Closure System for FDA Approval," *PR Newswire*, Apr. 11, 2005, pp. 1-3.
Gruchevsky, Marcie, Et Al., "Feature: Rapid Hemostasis Leading to Early Ambulation in Diagnostic Cardiac and Peripheral Angiography Patients Using V+Pad™ in Conjunction with Manual Digital Pressure at Florida Cath Lab," *Cath Lab Digest*, Jun. 2006, pp. 34-36, ISSN: 1073-2667, vol. 14, Issue 6.
Hursey, Francis X., "510(k) Summary; QuickClot," *On Site Gas Systems, Inc.*, May 29, 2002, pp. 1-3, Newington, CT., U.S.A.
Kern, Morton, "Letter from the Editor: Push, Pull, Click, Stitch: Managing Femoral Punctures," *Cath Lab Digest*, Jun. 2006, pp. 1-4, ISSN: 1073-2667, vol. 14, Issue 6.
Massat, Mary B., "Vascular Closure Devices," *Diagnostic & Invasive Cardiology*, Jan./Feb. 2003, pp. 1-5.
Melkerson, Mark N., "K013390; Trade/Device Name: QuikClot," *Department of Health & Human Services*, Mar. 27, 2002, pp. 1-3.
Niekraszewicz, Antoni, "Chitosan Medical Dressings," *Fibres & Textiles in Eastern Europe*, Jan./Dec. 2005, pp. 16-18, vol. 13, No. 6 (54).
Provost, Miriam C., "K023612; Trade/Device Name: Antimicrobial Barrier Wound Contact Dressing; Anitmicrobial Barrier Burn Wrap Dressing; Antimicrobial Barrier Burn Contact Dressing; Silverlon® Acute Burn Glove," *Department of Health & Human Services*, Oct. 28, 2002, pp. 1-5.
Rosenthal, A. Ralph, "K033666; Trade/Device Name: HemaDerm™," *Department of Health & Human Services*, Nov. 19, 2003, pp. 1-6.
Vascular Solutions, "A Quiet Groin.", http://www.vascularsolutions.com/products/duetttech/quietgroin.php, Sep. 28, 2006, p. 1, Minneapolis, MN., U.S.A.

Vascular Solutions, "Accelerated Hemostasis.", http://www.vascularsolutions.com/products/duetttech/acchemo.php, Sep. 28, 2006, p. 1, Minneapolis, MN., U.S.A.

Vascular Solutions, "Acolysis.", http://www.vascularsolutions.com/products/acolysis.php, Sep. 28, 2006, p. 1, Minneapolis, MN., U.S.A.

Vascular Solutions, "Complete Seal.", http://www.vascularsolutions.com/products/duetttech/completeseal.php, Sep. 28, 2006, p. 1, Minneapolis, MN., U.S.A.

Vascular Solutions, "D-Stat.", http://www.vascularsolutions.com/products/dstat.php, Sep. 28, 2006, pp. 1-2, Minneapolis, MN., U.S.A.

Vascular Solutions, "Diagnostic Duett Pro." http://www.vascularsolutions.com/products/diagnostic.php, Sep. 28, 2006, pp. 1-2, Minneapolis, MN., U.S.A.

Vascular Solutions, "Documented GP IIb/IIIa Results.", http://www.vascularsolutions.com/products/duetttech/docgp.php, Sep. 28, 2006, p. 1, Minneapolis, MN., U.S.A.

Vascular Solutions, "Duet", http://www.vascularsolutions.com/products/duetttech.php, Sep. 28, 2006, p. 1, Minneapolis, MN., U.S.A.

Vascular Solutions, "Duett Pro.", http://www.vascularsolutions.com/products/duettpro.php, Sep. 28, 2006, pp. 1-2, Minneapolis, MN., U.S.A.

Vascular Solutions, "Langston Dual Lumen Catheters.", http://www.vascularsolutions.com/products/langston.php, Sep. 28, 2006, p. 1, Minneapolis, MN., U.S.A.

Vascular Solutions, "Products.", http://www.vascularsolutions.com/products.php, Sep. 28, 2006, p. 1, Minneapolis, MN., U.S.A.

Vascular Solutions, "Pronto.", http://www.vascularsolutions.com/products/pronto.php, Sep. 28, 2006, pp. 1-2, Minneapolis, MN., U.S.A.

Vascular Solutions, "Reduced Cost", http://www.vascularsolutions.com/products/duetttech/reducedcost.php, Sep. 28, 2006, pp. 1-2, Minneapolis, MN., U.S.A.

Vascular Solutions, "Vari-Lase Endovenous Laser Therapy." http://www.vascularsolutions.com/products/varilase.php, Sep. 28, 2006, p. 1, Minneapolis, MN., U.S.A.

Witten, Celia M., "K984210; Trade Name: Silverlon™ Wound Packing Strips," *Department of Health & Human Services*, Jul. 14, 1999, pp. 1-6.

U.S. Appl. No. 11/671,448, filed Feb. 5, 2007, Bergin, et al.

Kapadia, Samir R., "The 6Fr Angio-Seal Arterial Closure Device: Results from a Multimember Prospective Registry," *The American Journal of Cardiology*, Mar. 15, 2001, pp. 789-791, vol. 87.

Kussmaul III, William G., "Rapid Arterial Hemostasis and Decreased Access Site Complications After Cardiac Catheterization and Angioplasty: Results of a Randomized Trial of a Novel Hemostatic Device," *JACC*, Jun. 1995, pp. 1685-1692, vol. 25, No. 7.

International Search Report for PCT/US2006/017348, Mar. 28, 2008 (mailing date), Innovasa Corporation.

Written Opinion for PCT/US2006/017348, Mar. 28, 2008 (mailing date), Innovasa Corporation.

International Search Report for PCT/US2007/079608, Apr. 11, 2008 (mailing date), Innovasa Corporation.

Written Opinion for PCT/US2007/079608, Apr. 11, 2008 (mailing date), Innovasa Corporation.

Office Action for U.S. Appl. No. 11/245,956 mailed on Sep. 24, 2008 (11 pages).

Office Action for U.S. Appl. No. 11/354,225 mailed on Sep. 25, 2008 (13 pages).

Office Action for U.S. Appl. No. 11/671,448 mailed on Jun. 23, 2009 (14 pages).

Office Action for U.S. Appl. No. 11/862,187 mailed on Jun. 23, 2009 (10 pages).

Siekman, Philip, "A Shrimp Bandage?", *FSB Magazine*, Jul./Aug. 2006, pp. 67-68.

\* cited by examiner

HEMOSTATIC WIRE GUIDED BANDAGE AND METHOD OF USE

REFERENCE TO RELATED APPLICATIONS

This application claims priority to United States Provisional Application filed on Jun. 7, 2005, assigned Ser. No. 60/688,510 and titled "Hemostatic Wire Guided Bandage," United States Provisional Application filed on Jun. 24, 2005, assigned Ser. No. 60/693,706 and titled "Vascular Puncture Sealing Device and Method of Use," United States Provisional Application filed on May 4, 2005, assigned Ser. No. 60/677,863 and titled "Vascular Closure System," and United States Provisional Application filed on Oct. 5, 2005, assigned Ser. No. 60/723,878 and titled "Vascular Puncture Sealing Mechanism and Method of Use." All four of said applications are incorporated herein by reference. This application is also a continuation-in-part of U.S. patent application Ser. No. 11/245,956, entitled "Hemostatic Wire Guided Bandage and Method of Use," filed Oct. 7, 2005, now abandoned which is incorporated herein by reference.

FIELD OF THE INVENTION

The invention is directed towards a wire guided hemostatic bandage normally placed subcutaneously and a method of using the same.

BACKGROUND OF THE INVENTION

Numerous medical diagnostic and therapeutic procedures require access to the internal organs of a living organism. Some of these procedures can be performed without traditional surgical incisions by utilizing catheter-based apparatus to enter blood vessels. Usually, catheter-based apparatus require a needle to be inserted through the skin and directed into a blood vessel. This provides a conduit for extending a metal or polymer guide wire through the needle and into the vasculature. After positioning the guide wire in the conduit, the needle can be removed and replaced with a hollow tube or catheter directed over the guide wire into the blood vessel. The tube or catheter provides access for administration of certain substances and/or for passage of additional equipment that will be used to perform manipulations within the vasculature or within other organ systems accessible through the vasculature.

To prevent bleeding upon completion of a catheter-based intravascular procedure, the catheter must be removed and the puncture site sealed. In the low-pressure environment of the venous system, a small needle puncture is readily sealed by the brief application of pressure to the site and application of a light dressing, such as a bandage. This method is widely utilized after needle stick procedures such as blood drawings.

However, when punctures are created with larger caliber apparatus (such as catheters) in the high-pressure environment of arteries, the puncture created will not readily seal with the application of brief pressure. Prolonged external pressure may be required for fifteen to thirty minutes and may lead to substantial discomfort at the puncture site for the patient and/or a significant failure rate with late bleeding and hematoma formation.

In the past, several methods have been proposed to address this problem. For instance, one prior apparatus utilizes a marker to indicate the position of the bandage with respect to the wound to be treated in order to position externally applied pressure at or near a puncture site. Another apparatus uses a pad which, when moistened by fluid from a wound, expands and exerts pressure against a wound.

Another apparatus utilizes laser energy directed through a balloon tipped catheter into the vascular tract and positioned just outside the outer wall of the blood vessel. The balloon is used to create a covering for the vascular puncture. The laser is used to create a laser "weld" or seal in the adjacent tissue.

Another apparatus uses both a balloon tipped catheter and an absorbable plug. The plug is used to occlude the vascular access tract and provide hemostasis. The balloon tipped catheter serves as a positioning anchor for antegrade insertion of the vascular plug and must be removed from the patient after plug deployment.

Yet another apparatus uses a balloon tipped catheter arranged so as to pass into the vascular lumen by means of the extant access sheath. After this procedure it is withdrawn to the intraluminal side of the blood vessel puncture to provide temporary hemostasis. A pro-coagulant slurry is then injected into the vascular access tract to promote coagulation. During this time, the balloon tipped catheter remains inflated. After a suitable period of time necessary to promote blood coagulation, the balloon tipped catheter is deflated and withdrawn from the access tract.

Each of these approaches has its own unique set of shortcomings. The prior apparatus lack both a means for precise positioning of a pressure-generating component against a puncture tract and a structure designed to optimize the pressure that is to be applied to such a site. Therefore, there is a need in the art for an apparatus that hemostatically closes a vascular puncture site without leaving a hematoma within the puncture tract, while minimizing patient discomfort. Ideally, such an apparatus would quickly, painlessly and reliably achieve hemostasis upon withdrawal of vascular catheters, and consequently reduce patient discomfort, staff time and the unfavorable failure rate associated with vascular hemostasis and the risk of hematoma formation.

SUMMARY OF THE INVENTION

Some embodiments of the invention provide an apparatus for achieving hemostasis in a puncture tract that is created during a medical procedure. The puncture typically extends from the epidermis to the vasculature in a living organism. In some embodiments, the apparatus includes (1) a plug for subcutaneous placement within the puncture tract, and (2) a delivery mechanism for delivering and maintaining the plug within the puncture tract until hemostasis is achieved. The apparatus also includes in some embodiments a lubricious sheath that is placed around the plug to facilitate the insertion of the plug into the puncture tract.

In some embodiments, the delivery mechanism and its associated plug are removed after hemostasis has been achieved. In this manner, the delivery mechanism and its associated plug act as a disposable bandage. The plug is the component of the disposable bandage that is inserted into the puncture tract to achieve hemostasis. The plug can have many shapes. Also, in some embodiments, the plug includes one or more materials (e.g., Chitosan) designed to promote coagulation and thereby achieve hemostasis. In some embodiments, the delivery mechanism allows an operator to apply pressure to maintain the plug in the puncture tract until hemostasis is achieved. In some embodiments, the delivery mechanism also occludes the opening of the puncture tract.

BRIEF DESCRIPTION OF THE DRAWINGS

The novel features of the invention are set forth in the appended claims. However, for purpose of explanation, several embodiments of the invention are set forth in the following Figures.

DETAILED DESCRIPTION OF THE INVENTION

Figure 1:
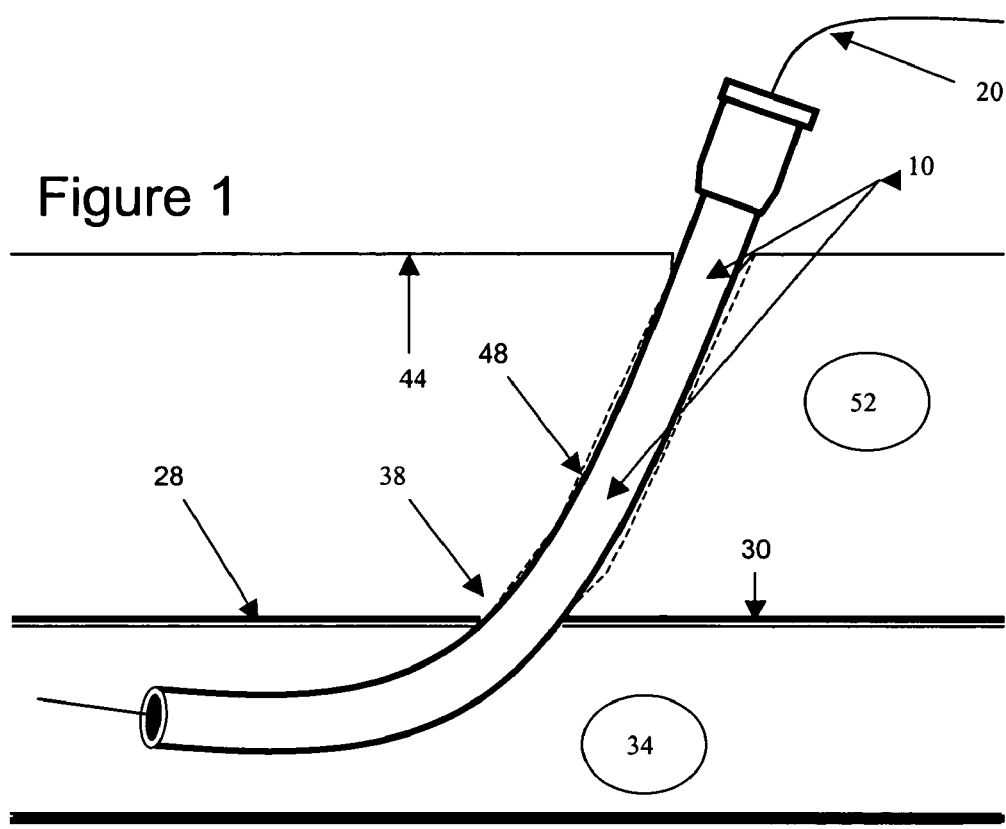
FIG. 1 illustrates a side elevation showing in cross section, a hemostasis sheath placed over a guide wire within a blood vessel through the epidermis and subcutaneous tissue of a living being.

In the following description, numerous details are set forth to provide a better understanding of the various embodiments of the invention. However, one of reasonable skill in the art will realize that the invention may be practiced without the use of the specific details presented herein. In some instances of describing the invention, well-known structures and apparatus may be shown in block diagram form to avoid obscuring the description of the invention with unnecessary detail. Therefore, the examples provided herein for clarification and understanding should not be read into and thereby limit the language of the claims.

Some embodiments of the invention provide an apparatus for achieving hemostasis in a puncture tract that is created during a medical procedure. The puncture typically extends from the epidermis to the vasculature in a living organism. In some embodiments, the apparatus includes (1) a plug for subcutaneous placement within the puncture tract, and (2) a delivery mechanism for delivering and maintaining the plug within the puncture tract until hemostasis is achieved. The apparatus also includes in some embodiments a lubricious sheath that is placed around the plug to facilitate the insertion of the plug into the puncture tract.

In some embodiments, the delivery mechanism and its associated plug are removed after hemostasis has been achieved. In this manner, the delivery mechanism and its associated plug act as a disposable bandage. The plug is the component of the disposable bandage that is inserted into the puncture tract to achieve hemostasis. The plug can have many shapes. Also, in some embodiments, the plug includes one or more materials (e.g., Chitosan) designed to promote coagulation and thereby achieves hemostasis. In some embodiments, the delivery mechanism allows an operator to apply pressure to maintain the plug in the puncture tract until hemostasis is achieved. In some embodiments, the delivery mechanism also occludes the opening of the puncture tract.

Several more detailed embodiments of the invention are discussed in Section III and IV. These embodiments provide a hemostatic bandage and a hemostatic wire-guided bandage delivery system. Before discussing these embodiments, it is helpful to understand relevant terminology and some environments in which the hemostatic bandage and its associated delivery system are used. Therefore, Section I presents relevant terminology, while Section II provides an overview of intravascular procedures, which are one type of procedure in which some embodiments can be used.

I. Terms and Terminology

An opening in the skin is called a percutaneous opening because it passes through the skin. The subcutaneous layer is the layer immediately below the skin, which is composed of the epidermal and dermal layers. The hole from the percutaneous opening to the blood vessel is the puncture tract or access tract. The opening in the blood vessel wall is a vascular puncture or vascular opening. The open space within the blood vessel is called the vascular lumen. As used in the following discussion, a "lumen" is an opening, such as the cavity of a tubular organ or the bore of a tube (as of a hollow needle or catheter). The term "bandage" is used generically to refer to an apparatus that assists in achieving hemostasis of a wound.

II. An Exemplary Intravascular Procedure

Some embodiments of the invention have particular utility when utilized in conjunction with intravascular procedures. Today, intravascular procedures are performed by many physicians, such as radiologists and cardiologists. Examples of intravascular procedures include angiography, angioplasty, vascular stenting and stent graft placement, arterial thrombectomy, arterial embolization, intra-arterial drug administration, etc. These procedures normally involve the insertion of a hollow needle (e.g., an 18 gauge thin walled needle) through the skin. The needle is advanced through the body tissue overlying a blood vessel and continued through the proximal side of the vascular wall until the distal tip of the needle enters the vascular lumen. A brisk return of blood through the needle hub signals entry of the needle into the vascular lumen.

Figure 2:
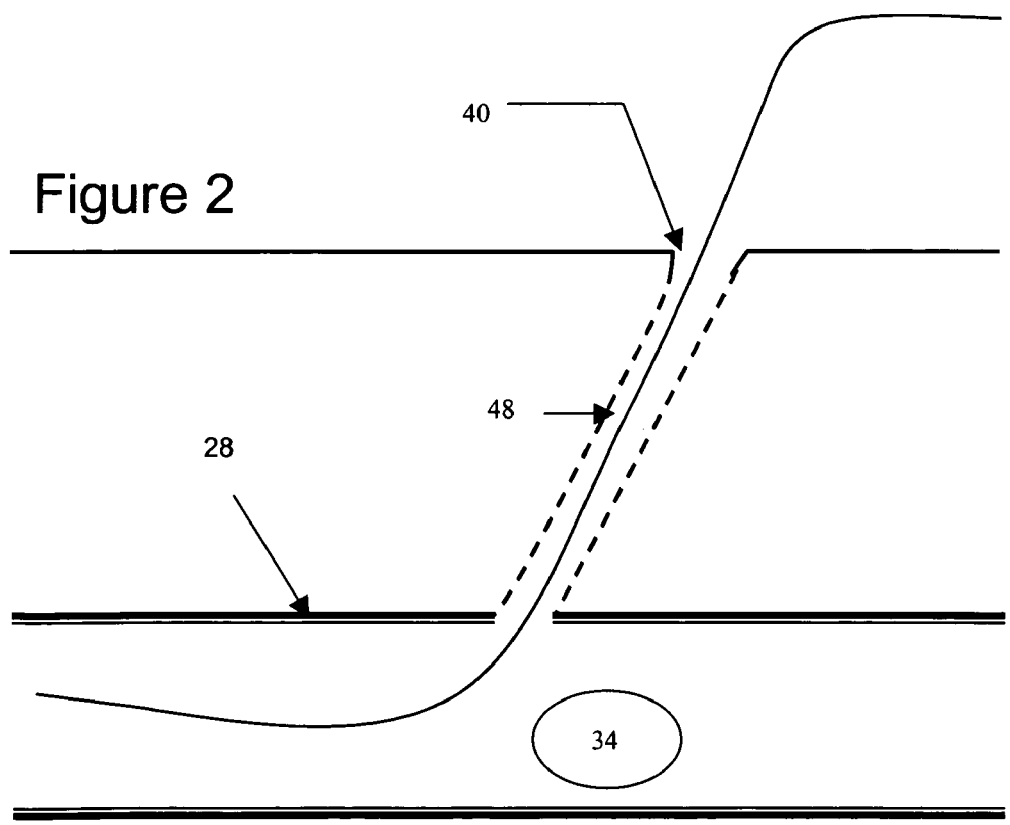
FIG. 2 illustrates a side elevation view showing in cross section, a guide wire in place with the hemostasis sheath removed.

FIGS. 1 and 2 illustrate an exemplary intravascular procedure that commonly uses an access sheath 10 placed in the access tract 48 to facilitate entry into the vascular lumen 34 by diagnostic and therapeutic tools. FIG. 1 illustrates the hemostasis access sheath 10 threaded onto a guide wire 20 and placed within the access tract 48.

To install the access sheath 10, the operator first creates an access path to the blood vessel 28 by cutting a percutaneous opening 40 in the epidermal layer 44 at a point that is favorable to accessing the blood vessel 28. A needle (or other cutting tool) is typically advanced through a percutaneous opening 40, an epidermal layer 44, a subcutaneous layer 52 and a vascular wall 30. It continues through the vascular wall 30 (creating a vascular puncture 38) and into a vascular lumen 34 of a blood vessel 28. This creates the access tract 48.

After creating the access tract 48, the operator typically threads a guidewire 20 longitudinally through the needle.

After positioning the guidewire 20 within the access tract 48, the needle may be removed while maintaining the guidewire 20 in position. Normally, an access sheath 10 is later placed within the access tract 48 to prevent the tract 48 from closing during the procedure. The access sheath 10 is typically threaded onto the guidewire 20 and inserted into the access tract 48, using the guidewire 20 to precisely position the sheath 10 into place. When positioned at its final location, one end of the sheath 10 is within the vascular lumen 34 while the opposing end is outside of the organism. Once the access sheath 10 is in place, other apparatus and/or materials can pass through the access sheath 10 and advance into the blood vessel 28 to the area of interest within the body, in order to perform the intravascular procedure.

Upon completion of the intravascular procedure, the catheters and other apparatus used in the procedure are removed from the blood vessel 28. This is generally followed by the removal of the sheath 10 over the guide wire 20, leaving the guide wire 20 in place within the access tract 48 and leaving the access tract 48 open. FIG. 2 presents a longitudinal cross-sectional side view of the access tract 48 with the guidewire 20 in place after the removal of the access sheath 10.

The removal of tools from the access tract 48 causes the access tract to gradually close upon any objects remaining within the tract 48. If hemostasis is not quickly attained, vigorous bleeding can occur. Therefore, the vascular puncture 38 and the access tract 48 must be sealed as quickly and as efficiently as possible. One method of doing so uses a hemostatic wire guided bandage delivery and placement apparatus of some embodiments of the invention.

III. Hemostatic Bandage and Wire-Guided Delivery System for Delivering the Hemostatic Bandage in a Puncture Tract Some embodiments provide a hemostatic bandage for achieving hemostasis in a puncture tract that is created during a medical procedure. Some embodiments also include a wire-guided delivery mechanism for delivering the bandage into the puncture tract and for maintaining the bandage in the puncture tract until hemostasis is achieved. In some embodiments, the mechanism not only positions the bandage, but also occludes the opening of the puncture tract. Although some embodiments of a hemostatic wire guided bandage delivery and placement apparatus achieve hemostasis at or near a vascular puncture site in a living organism, the apparatus' construction and use also has widespread applicability in analogous non-vascular settings.

Figure 3:
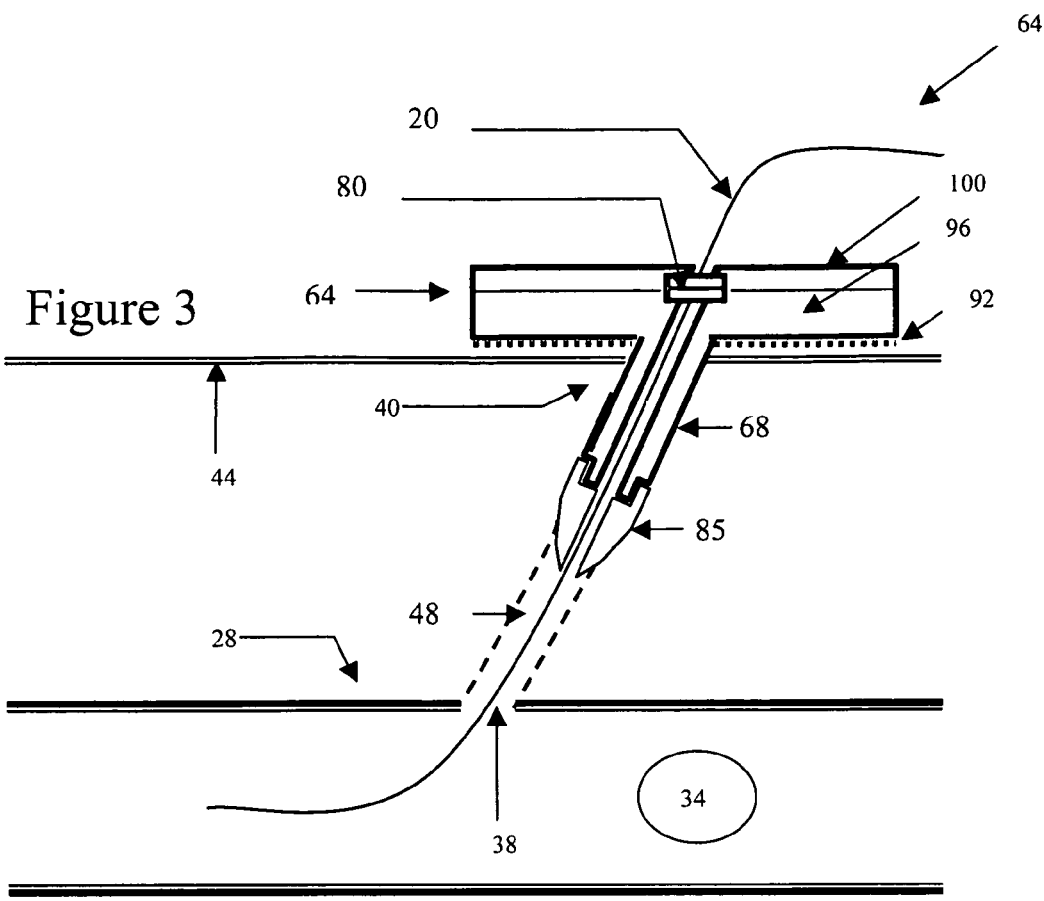
FIG. 3 illustrates a side elevation view showing in cross section, an occlusive plug and the hemostatic bandage being passed over the guidewire and into the puncture wound.
Figure 4:
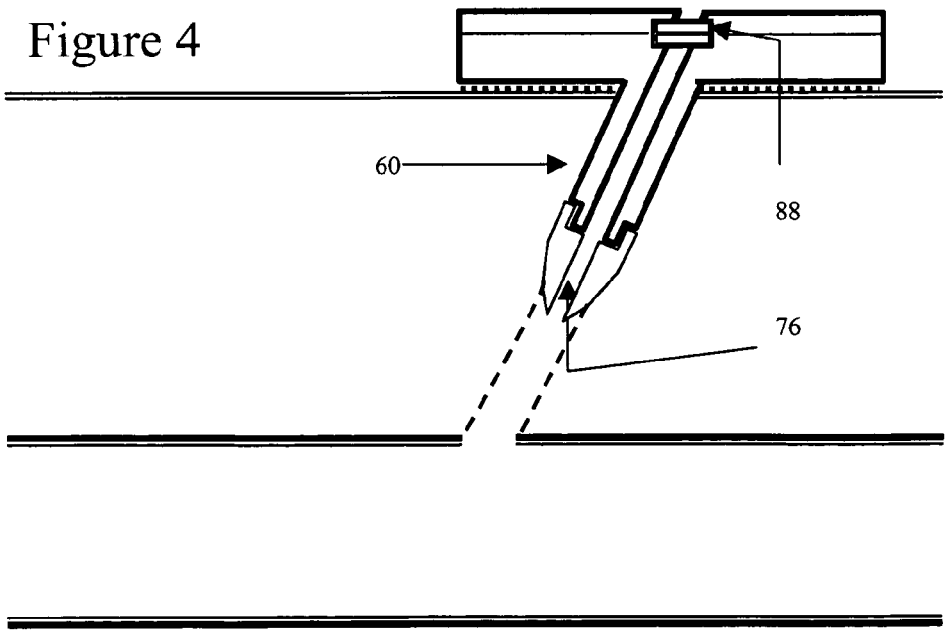
FIG. 4 illustrates a side elevation view showing in cross section, the occlusive plug in place with the guide wire removed and the hemostatic bandage secured within the puncture tract.
Figure 5:
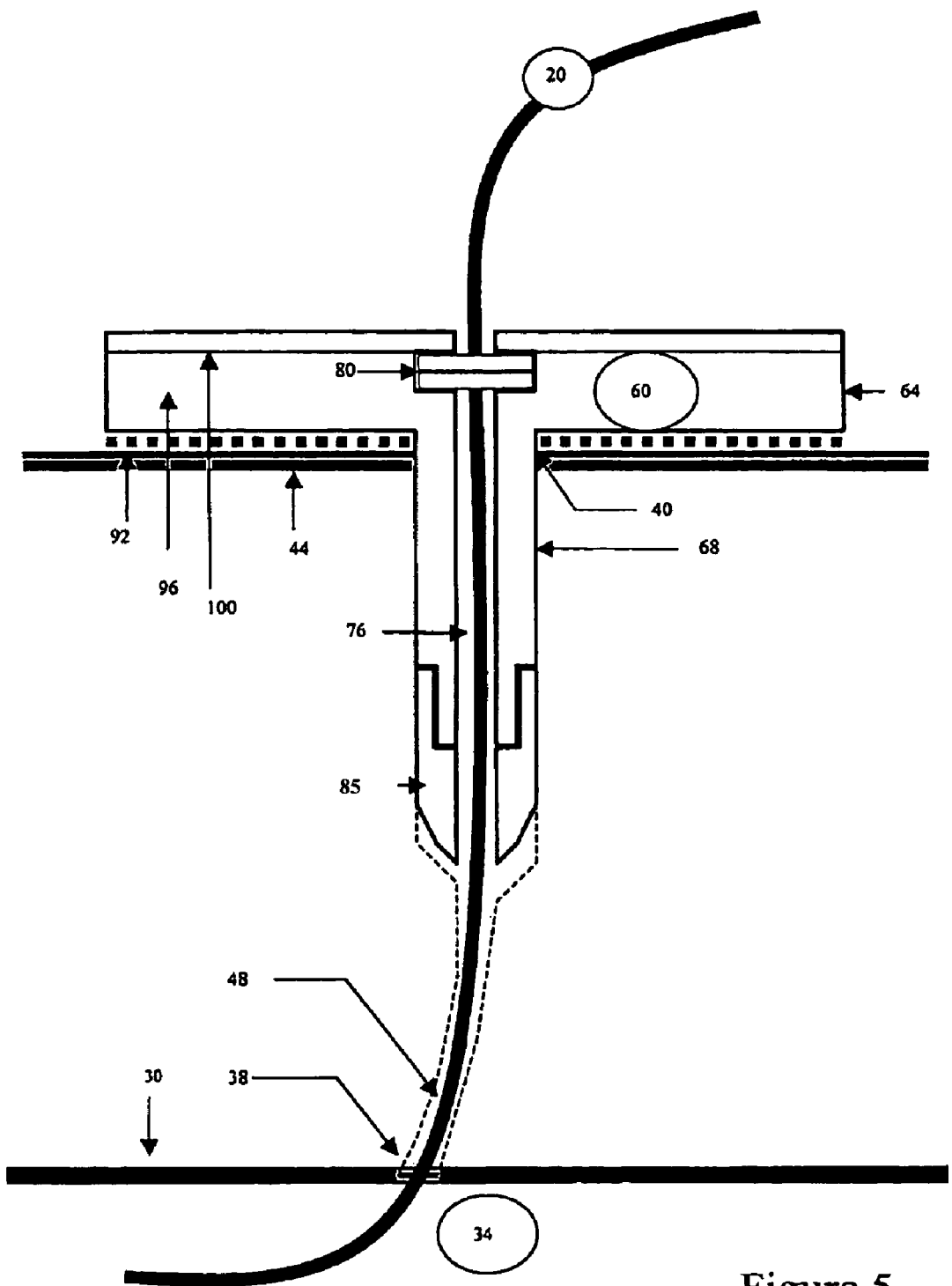
FIG. 5 illustrates a side elevation view of the component parts of the occlusive plug.

FIGS. 3 through 5 illustrate a hemostatic apparatus 60 of some embodiments of the invention. This apparatus includes a hemostatic bandage and its associated wire guided delivery apparatus. As shown in FIG. 3, the apparatus 60 includes (1) a cover pad 64, (2) a stem 68 affixed to the cover pad 64 and extending at a angle downwards from the bottom side of the cover pad 64, (3) a bandage 85 attached to the distal end of the stem 68, and (4) a central lumen 76 defined from the top of the cover pad downwards through the center of the stem 68 and through the center of the bandage 85. As shown in this figure, the cover pad includes a hemostatic valve 80.

As shown in FIG. 3, the apparatus 60 positions the bandage 85 subcutaneously to provide hemostasis within a puncture tract. In use, the cover pad of the apparatus 60 covers and/or occludes the access tract 48 percutaneously. The cover pad's hemostatic valve prevents blood from flowing back through the central lumen and out of the patient, while allowing for the passage of the guidewire 20 through the central lumen.

The stem 68 positions the bandage 85 within the access tract 48 to achieve hemostasis. As mentioned above, the stem extends downwards at an angle from the bottom side of the cover pad 64. This angle corresponds to the angle of the puncture tract. In some embodiments, the angle at which the stem extends downwards from the cover pad is adjustable to match angle of the puncture tract.

While FIG. 3 presents the guidewire 20 threaded through the apparatus 60, FIG. 4 presents the apparatus 60 after the guidewire 20 has been removed. The guidewire 20 is used to properly guide the bandage 85 as the apparatus 60 is advanced into the access tract 48. After the apparatus 60 is in place, the guidewire 20 may be removed, as shown in FIG. 4. Its removal from the access tract 48 causes the access tract to gradually close further.

The cover pad 64, hemostatic valve 80, a stem 68 and bandage 85 of the apparatus 60 are discussed in detail in Section A, immediately below. This discussion is followed in Section B by a description of how the apparatus 60 is used in some embodiments to place a hemostasis bandage subcutaneously within a puncture tract.

A. The Components of a Bandage Delivery and Placement Apparatus

1. The Cover Pad

In some embodiments, the cover pad 64 provides a mechanism (1) to push the stem 68 into the access tract 48, (2) to occlude the percutaneous opening 40, and (3) affix the apparatus 60 to the epidermal layer 44 during recovery. FIG. 5 presents a more detailed view of the apparatus 60. As shown in this figure, the apparatus 60 in some embodiments includes a multi-layered cover pad 64. The layers include a first adhesive layer 92, a second central layer 96 and a third surface layer 100. The cover pad in some embodiments includes a fourth layer (not shown in FIG. 5) that covers the first adhesive layer 92 as further described below. Although FIG. 5 shows a particular multi-layered cover pad, a person skilled in the art will realize that the cover pad 64 in other embodiments might be constructed differently (e.g., with more or less layers).

As mentioned above, the first layer 92 of the cover pad 64 in some embodiments is an adhesive layer that is applied to the bottom side of the second central layer 96. The first adhesive layer 92 is covered by a fourth layer (not shown) when the bandage has not been deployed. The fourth layer protects the adhesive layer from degradation before the bandage has been deployed. As further described below, the fourth layer is removed from the first layer 92 when the bandage is being deployed, in order to enable the first layer to affix the apparatus 60 to the patient's skin during the operation.

The second layer 96 has a lumen 88 defined about the central lumen 76, which passes through the second layer. The hemostatic valve 80 is seated with the second lumen 88, which is larger than, and concentric to, the central lumen 76 and is shaped to receive the valve 80. With the valve 80 seated in the second lumen 88, the third layer 100 covers the second layer 96 (including the valve 80) to immobilize the valve 80 within the second lumen 88. The third layer 100 contains a third lumen 101 that is concentric to the central lumen 76 and shaped to cooperate with and receive a portion of the hemostatic valve 80 seated in the second lumen 88.

Figure 6:
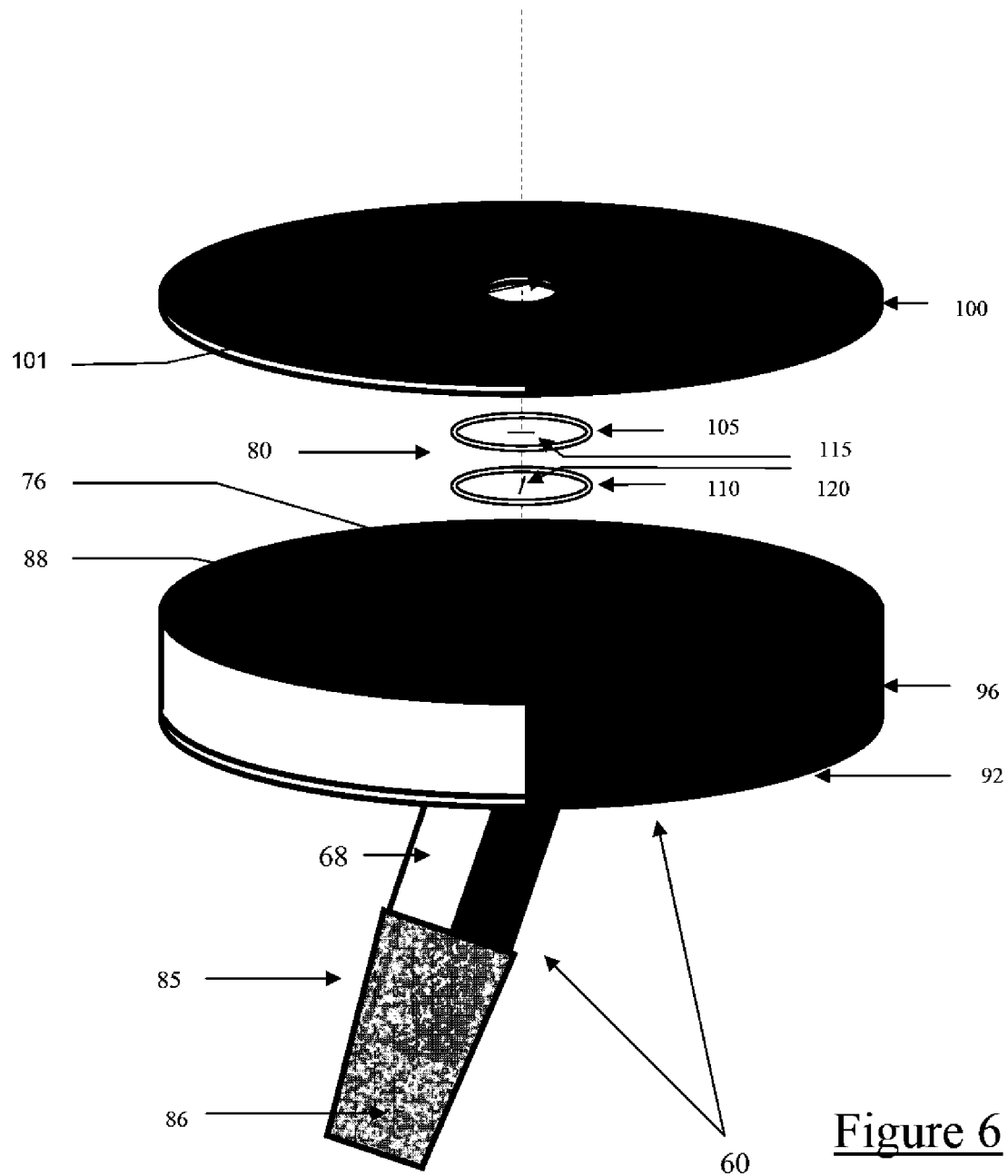
FIG. 6 illustrates an oblique three dimensional exploded view of the component parts of the occlusive plug.

FIG. 6 illustrates an exploded view of the cover pad 64 of some embodiments of the invention. As shown in this figure, the second lumen 88 of the second central layer 96 is larger than the third lumen 101 of the third layer 100. This figure also shows that in some embodiments the hemostatic valve 80 is formed by two circular pads 105 and 110.

The circular pads 105 and 110 are formed from a soft rubber material in some embodiments, while they might be formed by other materials in other embodiments. The pads have two slits 115 and 120 at a 90° angle with each other. These two slits allow the guide wire 20 to pass through the central lumen 76. However, the 90° arrangement of the slits plus the composition of the pads 105 and 110 limit the back flow of blood from the central lumen. Although the valve 80 is formed by two pads 105 and 110 in some embodiments, one of ordinary skill will realize that the valve 80 is formed differently (e.g., with different number of pads, different composition for the pads, different shaped pads, etc.) in other embodiments.

2. The Stem

As mentioned above, the stem 68 allows the bandage 85 affixed to the stem 68 to be placed in the subcutaneous tissue and within the access tract 48. In some embodiments, the stem 68 is roughly cylindrical and includes a proximal end and an opposing distal end. The proximal end is affixed to the cover pad 64. The distal end cooperates with the bandage 85 placed subcutaneously within the access tract 48. In different versions of the apparatus 60, the stem 68 may have different lengths, in order to position the bandage 85 at different depths within the access tract 48 based upon patient's circumstances. Alternatively, in some embodiments, the stem 68 is capable of different lengths by means of telescoping the stem. In other embodiments, the stem 68 may be sectioned and joined together, one section at a time, to create an appropriate length for each individual need.

The stem 68 allows the bandage 85 to be placed within the access tract 48 without causing the bandage 85 to flatten near the epidermal layer 44. In so doing, the bandage 85 is placed closer to the vascular puncture 38 and the chance of hematoma or other undesirable effects is reduced.

3. The Bandage

As mentioned above, the bandage 85 is located at the distal end of the stem 68. The bandage serves to occlude the access tract 48 and provide hemostasis within the access tract 48 without undesirable side effects. In some embodiments, the bandage 85 is a plug that contains a central lumen designed to accept the guidewire 20 and is a component of the delivery apparatus 60. As shown in FIG. 3-6, the plug 85 has a tapered tip in some embodiments to facilitate entry into the puncture tracts. The depth at which the plug 85 is positioned in the access tract 48 will be approximately the length of the stem 68. In some embodiments, the circumference of the plug 68 is approximately the diameter of the access tract 48.

Some of the embodiments of the bandage 85 may be made from, or coated with, one or more coagulating materials. Coagulating agents facilitate coagulation and hemostasis. One such pro-coagulation material is Chitosan. By including one or more pro-coagulating agents within the bandage, hemostasis is achieved earlier than it would be otherwise achievable. By varying the composition of the bandage 85, the hemostasis rate may be controlled or varied. In this manner, the hemostasis rate may be controlled to fit the needs of each individual circumstance.

B. Method of Use

As discussed previously, removing the access sheath 10 from the access tract 48 at the completion of an intravascular procedure causes the access tract 48 to naturally collapse onto the guidewire 20. Therefore, the apparatus 60 should be inserted into the access tract 48 before the tissue collapses onto the access tract 48. To be most effective, the operator should be able to insert the apparatus 60 quickly, easily and efficiently.

At the conclusion of an intravascular medical procedure, most of the instrumentation used in the procedure is typically removed from the blood vessel and the access tract. For instance, all the instrumentation except the access sheath 10 might be removed from the blood vessel and the access tract. Next, a guidewire 20 is re-inserted into the access tract (e.g., re-inserted through the access sheath) and the sheath 10 is then removed.

To insert the apparatus 60, the apparatus is first threaded onto the guidewire 20 by inserting the side of the guidewire 20 that is out of the patient through the hole in the tip of the plug 85, through the central lumen 76, through the slits 115 and 120 of the valve 80, and out of the cover pad. The cover for the adhesive layer 92 of the pad 64 is removed to reveal the adhesive layer 92. Next, the apparatus 60 is advanced into the access tract 48 until the bandage 85 is properly placed subcutaneously and the adhesive layer 92 comes in contact with the epidermis 44. With the adhesive layer exposed, the cover pad 64 can firmly adhere to the epidermal layer 44 to prevent the bandage 85 from moving within the access tract 48. With the apparatus 60 properly positioned, the guidewire 20 can be removed, as shown in FIG. 4.

With the apparatus 60 in place, the hemostasis valve 80 prevents back bleeding through the central lumen 76. The bandage 85 acts to seal the remaining portion of the access tract. By placing the apparatus 60 within the access tract 48, the bandage 85 and the cover pad 64 both obstruct the flow of blood from the vascular puncture 38.

In some embodiments, the bandage 85 is coated with, contains, or is completely composed of Chitosan or other pro-coagulant material. The use of coagulating agents in the bandage 85 further impedes the blood flow. Next, the removal of the guidewire 20 causes the access tract 48 to collapse. Also, the tissue exerts force on the tapered tip of the bandage to close the hole at this tip. The insertion of the bandage, the use of the coagulating agent, and the collapse of the tissue restrict the flow of blood from the blood vessel 28 and thereby quickly and efficiently result in hemostasis. To achieve hemostasis, a physician might also exert minimal pressure on the cover pad in some cases for a small duration of time (e.g., thirty to sixty seconds). Also, the bandage 85 has to remain in the patient for a suitable amount of time to achieve hemostasis. This amount can be as little as 30 to 60 minutes in some cases.

After a suitable period to allow for recovery and healing, the bandage 85 is removed from the living organism by pulling the cover pad away from the patient. After the removal of apparatus 60, a light topical dressing is then applied to the wound.

IV. Hemostatic Bandage with Lubricious Sheath

Figure 11:
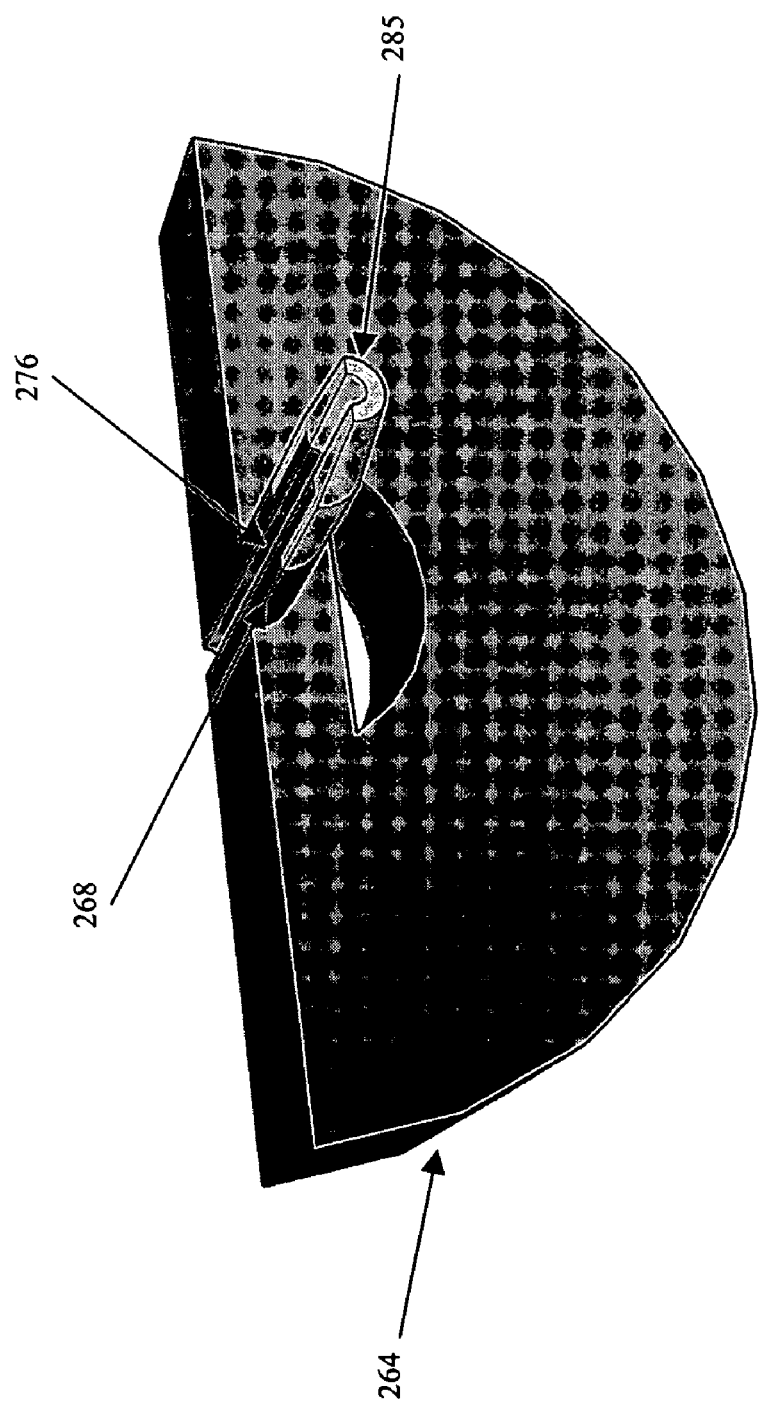
FIG. 11 illustrates a cross sectional view of the cover pad and bandage of the hemostatic apparatus of some embodiments.

FIGS. 7-11 illustrate another example of a hemostatic apparatus 260 of some embodiments of the invention. The hemostatic apparatus 260 has many of the same features as the hemostatic apparatus 60 illustrated in FIGS. 3-5. For instance, as illustrated in FIGS. 7-10, the apparatus 260 includes (1) a cover pad 264, (2) a stem 268 affixed to the cover pad 264 and extending downwards from the bottom side of the cover pad 264, and (3) a bandage 285 attached to the distal end of the stem 268. Like the bandage 85 of apparatus 60, the bandage 285 of apparatus 260 has a tapered tip. The bandage 285 or its tapered tip is coated with, contains, or is completely composed of Chitosan or other pro-coagulant material in some embodiments. Also, like the apparatus 60, the apparatus 260 has a central lumen 276 defined from the top of the cover pad downwards through the center of the stem 268 and through the center of the bandage 285, as illustrated in FIG. 11.

Figure 7:
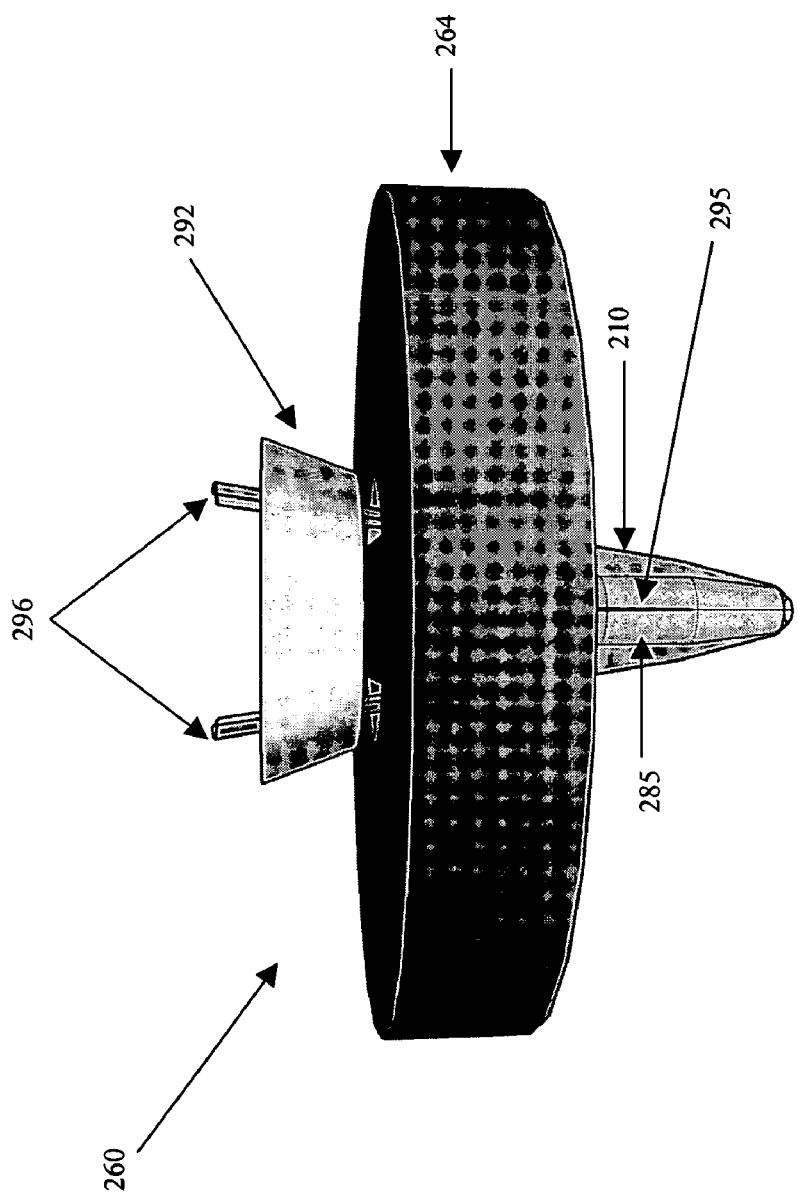
FIG. 7 illustrates side plan view of the hemostatic apparatus according to some embodiments of the invention.
Figure 8:
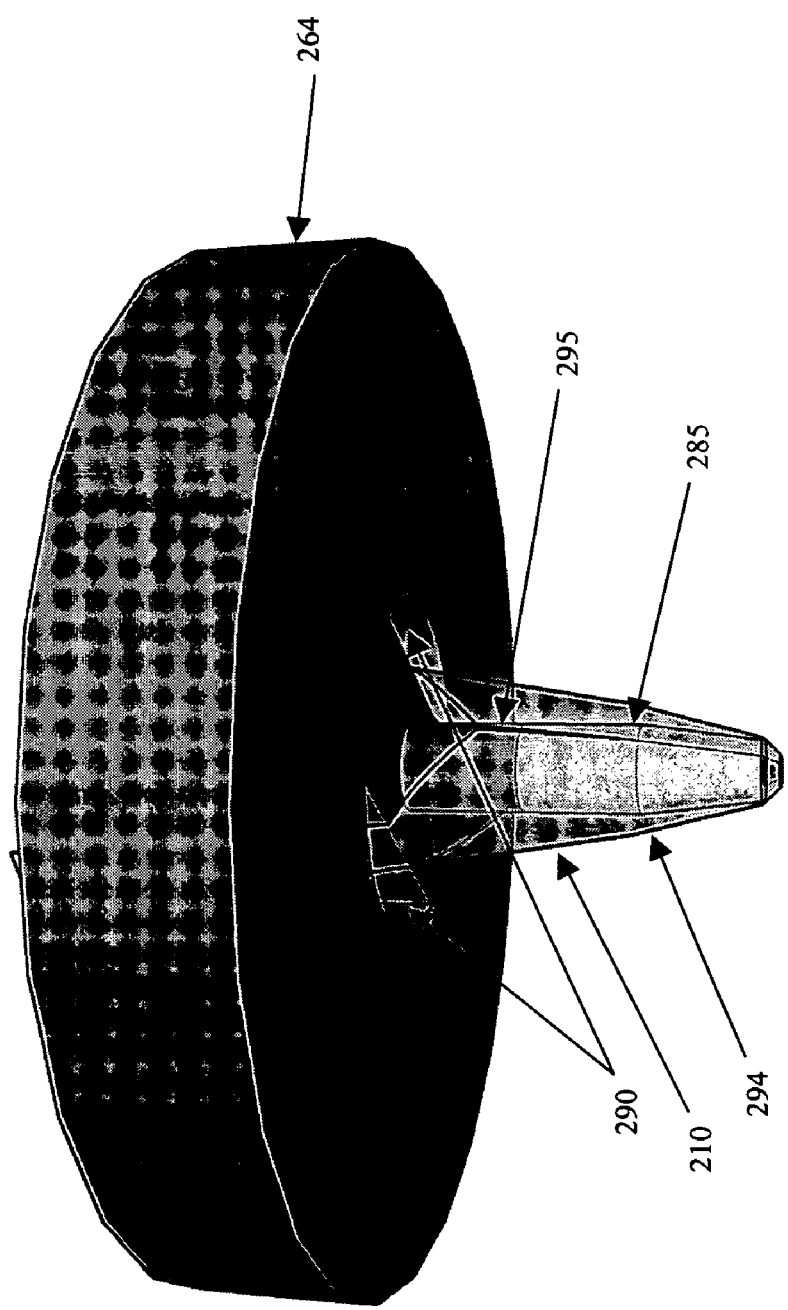
FIG. 8 illustrates a bottom perspective view of the hemostatic apparatus of some embodiments.
Figure 9:
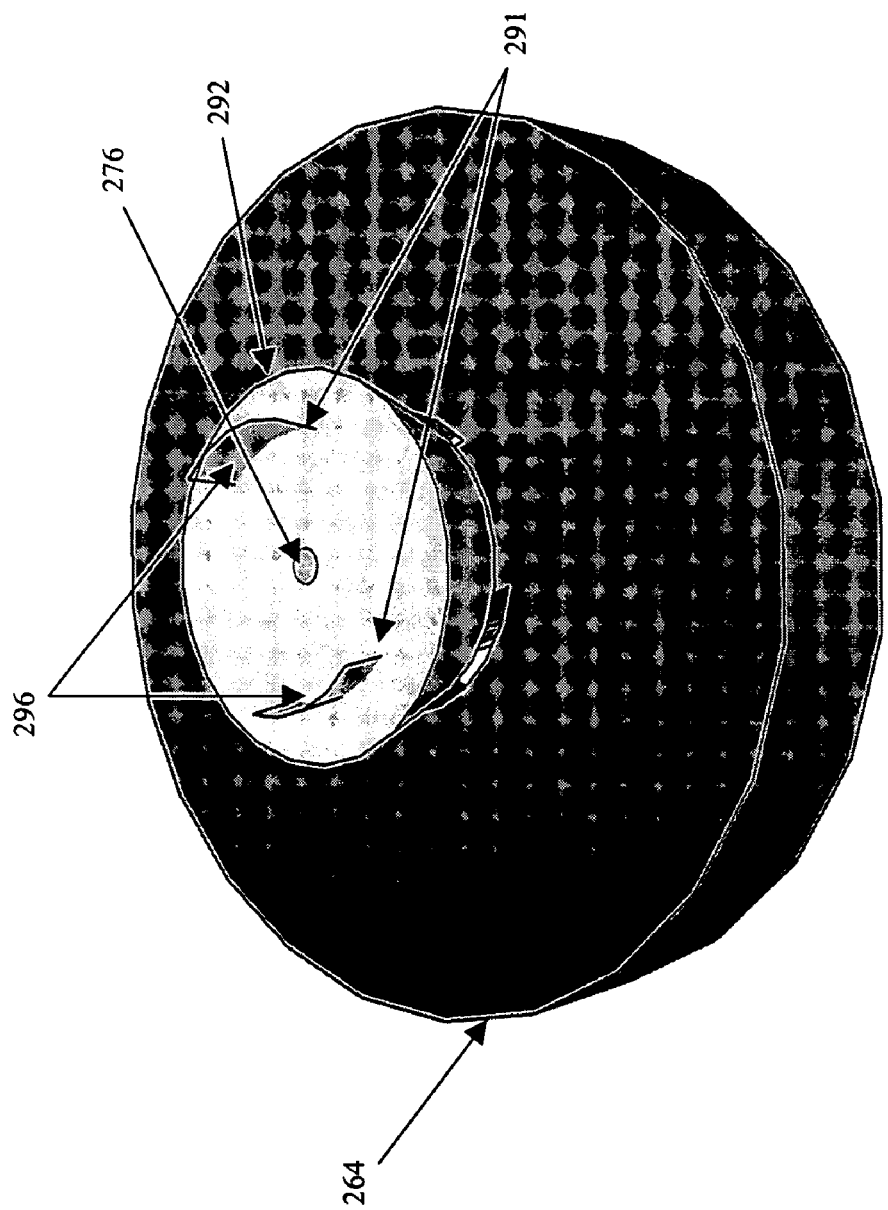
FIG. 9 illustrates a top perspective view of the hemostatic apparatus of some embodiments.
Figure 10:
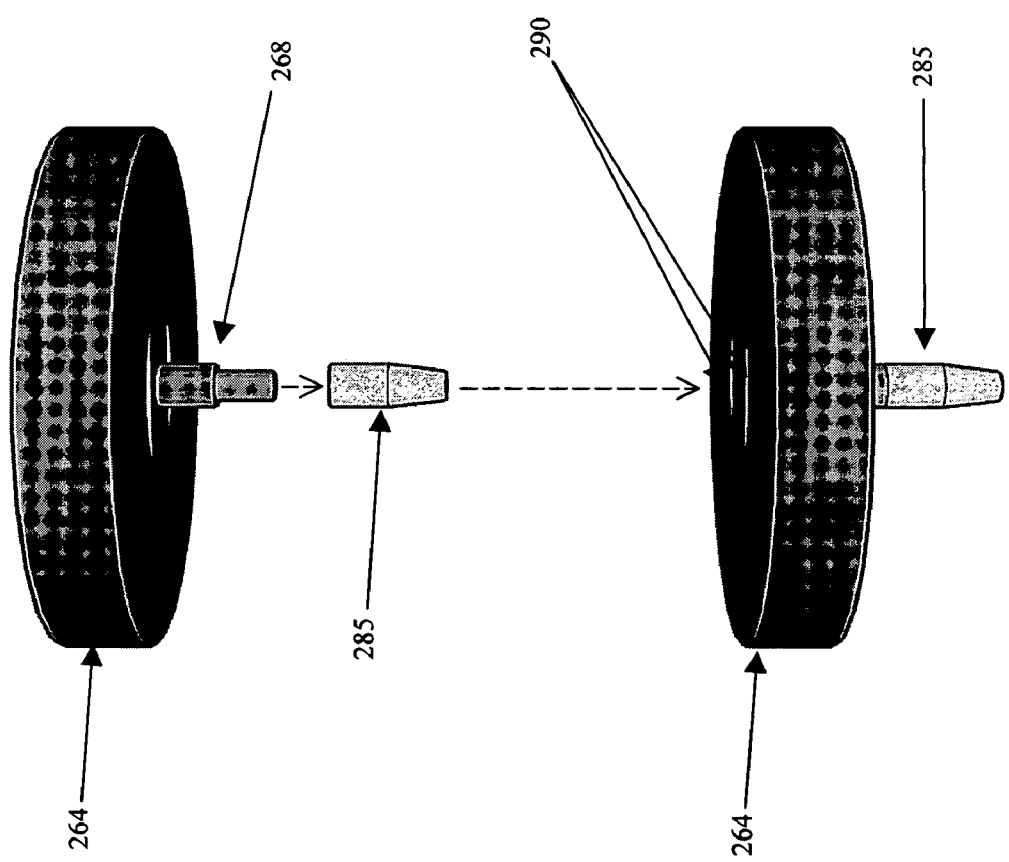
FIG. 10 illustrates an exploded and compacted view of the hemostatic apparatus of some embodiments.

In addition to these components, the apparatus 260 includes (1) two slots 290 in the cover pad 264, (2) a sheath 210, and (3) a holding pad 292 with two slots 291. The sheath 210 is coated with, or is composed partially or entirely of, a lubricious material, such as a hydrophilic polymeric film or other hydrophilic material. The lubricious sheath 210 has a hollow tip 294 that surrounds the bandage 285 (i.e., surrounds the tip). The sheath also has two flaring fingers 296 that extend from the hollow tip 294. As illustrated in FIGS. 7-9, these two fingers 296 pass through the two slots 290 of the cover pad 264 and the two slots 291 of the holding pad 292, which rests on top of the cover pad 264. In this manner, the two fingers 296 maintain the lubricious sheath's hollow tip around the bandage 285. The central lumen 276 of the apparatus 260 is defined through the sheath 210 and the holding pad 292.

The apparatus 260 of FIGS. 7-9 operates in a similar manner to the apparatus 60 of FIGS. 3-5. Specifically, the stem 268 and the bandage 285 of the apparatus 260 is pushed into a puncture tract by passing the central lumen 276 of the apparatus 260 over a guidewire that is positioned in the access tract.

The lubricious sheath 210 assists in positioning the bandage 285 into the puncture tract. Without this sheath, a surgical-team member might have a hard time inserting the bandage 285 into the puncture tract. However, with the sheath, the bandage can be inserted much easier into the tract, as the lubricious sheath becomes slick when it contacts liquids in the tract.

Once the bandage 285 has been placed in its desired position within the tract, the operator removes the sheath 210 from the puncture tract. The sheath 210 has slits 295 on the exterior surface of its hollow tip 294. To remove the sheath 210 from the puncture tract, the operator pulls the holding pad 292 away from the cover pad 264. This pulling causes the hollow tip 294 to tear typically along the position of the slits 295. This tearing breaks the enclosure of the tip 294 around the bandage 285, and thereby allows the sheath to slide out of the puncture tract.

With the sheath removed, the pro-coagulant material of the bandage 285 achieves hemostasis in a few minutes. Specifically, as mentioned above, the bandage 285 is coated with, contains, or is completely composed of Chitosan or other pro-coagulant material in some embodiments. The use of coagulating agents in the bandage 285 impedes the blood flow almost immediately after the removal of the sheath. In addition, before or after the removal of the sheath, the guidewire is removed, and this removal causes the access tract to collapse. Also, the tissue exerts force on the tapered tip of the bandage to close the hole at this tip. Accordingly, the insertion of the bandage, the use of the coagulating agent, and the collapse of the tissue restrict the flow of blood from the blood vessel and thereby quickly and efficiently result in hemostasis.

To achieve hemostasis, a physician might also exert minimal pressure on the cover pad in some cases for a small duration of time (e.g., thirty to sixty seconds). Also, the bandage 285 has to remain in the patient for a suitable amount of time to achieve hemostasis. This amount can be as little as 30 to 60 minutes in some cases. After a suitable period to allow for recovery and healing, the bandage 285 is removed from the living organism by pulling the cover pad away from the patient. After the removal of apparatus 260, a light topical dressing might be applied to the wound.

The delivery apparatus and bandage of some embodiments constitute a significant advance in the fields of cardiology, radiology and vascular surgery as it significantly improves upon the art by providing an effective means of completely sealing a vascular access puncture site, even in anti-coagulated patients, without bleeding and hematoma formation.

Compared with the topical application of a bandage as used in the prior art without the precise guide wire directed positioning of the invention's insertion bandage tip, the probability of hematoma formation and the need for prolonged application of external pressure is greatly reduced by using the apparatus. The apparatus will reduce patient discomfort, improve sheath related complication rates due to bleeding and hematoma formation, eliminate intra-arterial trauma, reduce hospitalization time and allow rapid mobilization and earlier discharge of patients following catheter based vascular procedures.

While the invention has been described herein with reference to numerous specific details, one of ordinary skill in the art will recognize that the invention can be embodied in forms without departing from the spirit of the invention. For instance, in some cases, the invention's bandage will be used for hemostasis of the radial artery in the wrist. The same guide wire delivery will apply, but the device will be secured by a wrist strap rather than an adhesive bandage. In addition, in the case of the very superficial radial puncture, the device can be placed on but not within a subcutaneous tract, as the tract at the radial site is very short and cannot be entered with a device. Thus, one of ordinary skill in the art would understand that the invention is not to be limited by the illustrative details contained herein, but rather is to be defined by the appended claims.

What is claimed is:

1. A method of achieving hemostasis in a puncture tract that is created during a medical procedure on a patient, the method comprising:
    inserting a guide wire into the puncture tract;
    sliding a bandage and a delivery mechanism coupled to the bandage over the guide wire in order to insert the bandage and at least a portion of the delivery mechanism into the puncture tract;
    after sliding the bandage and the delivery mechanism over the guide wire, removing the guide wire, wherein removing the guide wire causes a portion of the puncture tract to collapse;
    applying pressure to the delivery mechanism while maintaining the bandage in the puncture tract; and
    after removing the guide wire, pulling the delivery mechanism away from the puncture tract in order to remove the bandage from the puncture tract after a period of time, wherein said delivery mechanism is directly and fixedly coupled to the bandage while delivering and maintaining the bandage in the puncture tract and while removing the bandage from the puncture tract.

2. The method of claim 1, wherein the removing of the bandage from the puncture tract includes removing the bandage from the puncture tract after achieving hemostasis.

3. The method of claim 1, wherein the bandage includes at least one coagulating material.

4. The method of claim 1 further comprising passing the wire through a valve located in a passageway of the delivery mechanism, said valve preventing blood from flowing out of the patient through the passageway while allowing the wire to pass through the passageway.

5. The method of claim 1 further comprising affixing the delivery mechanism to the patient while the bandage is within the puncture tract.

6. The method of claim 1, wherein the bandage has a tapered tip.

7. The method of claim 1, wherein the puncture tract terminates at a vascular puncture, wherein when the bandage is inserted into the puncture tract, the bandage does not reach the vascular puncture.

8. The method of claim 1, wherein the delivery mechanism further includes a stem, the bandage being located on a distal end of the stem, and, when fully deployed to promote hemostasis, a total length of the bandage and the stem being less than a length of the puncture tract.

9. The method of claim 8, wherein the bandage surrounds a portion of the stem and the stem further includes a lumen.

10. A method of operating a hemostatic device comprising a bandage and a delivery mechanism, said delivery mechanism comprising a pad having a surface and a stem coupled to the bandage, the method comprising:
   forming an opening and an access tract in skin of a patient;
   forming a vascular puncture at an end of the access tract, the vascular puncture extending through a wall of a vessel;
   directing the stem of the delivery mechanism toward a puncture tract to insert the bandage into the puncture tract but not through a vascular puncture, wherein a total length of the bandage and the stem of the delivery mechanism, when the bandage is fully deployed in the access tract to promote hemostasis, is less than the distance from the opening to the vascular puncture;
   maintaining the surface of the pad outside the puncture tract;
   applying pressure to the surface of the pad in order to apply pressure which maintains the bandage in the puncture tract; and
   after a period of time, pulling the delivery mechanism away from the puncture tract in order to remove the bandage from the puncture tract, said delivery mechanism being fixedly coupled to the bandage while maintaining the bandage in the puncture tract and while pulling the delivery mechanism away from the puncture tract.

11. The method of claim 10, wherein when the bandage is fully deployed into the puncture tract, the bandage does not reach the vascular puncture.

12. The method of claim 10, wherein pulling the delivery mechanism away from the puncture tract includes pulling the delivery mechanism away from the puncture tract after achieving hemostasis.

13. The method of claim 10, wherein the bandage includes:
   a tapered tip on a distal end of the bandage;
   a central lumen; and
   at least one coagulating material.

14. The method of claim 10, further including securing the delivery mechanism to prevent the bandage from moving within the puncture tract.

15. The method of claim 10, wherein the bandage is located on a distal end of the stem.

16. The method of claim 10, further including:
   prior to directing the delivery mechanism toward the puncture tract, placing a guide wire through the puncture tract and the vascular puncture;
   threading the delivery mechanism onto the guide wire; and
   after the bandage has been inserted into the puncture tract but before removing the bandage from the puncture tract, removing the guide wire such that a portion of the puncture tract collapses.

17. A method of performing a medical operation, comprising:
   forming an access tract in skin of a patient through a percutaneous opening;
   forming a vascular puncture at an end of the access tract, the vascular puncture extending through a wall of a vessel;
   placing a guide wire through the access tract and the vascular puncture and into the vessel;
   threading an apparatus onto the guide wire, the apparatus including a bandage on a distal end of the apparatus, the apparatus further including a mechanism to deliver the bandage;
   advancing the apparatus into the access tract;
   stopping advancement of the apparatus prior to the apparatus reaching the wall of the vessel so that the bandage is positioned within the access tract proximal to the vascular puncture, at least a portion of the mechanism being positioned outside of the patient;
   while the apparatus is positioned in the access tract, removing the guide wire such that a portion of the access tract collapses; and
   without disconnecting the mechanism from the bandage, removing the bandage from the access tract through the percutaneous opening.

18. The method of claim 17, further including applying pressure to the mechanism while maintaining the bandage in the puncture tract.

19. The method of claim 17, wherein the bandage includes a tapered tip and a lumen configured to receive the guide wire.

20. The method of claim 17, wherein the mechanism further includes a stem, the bandage being located on a distal end of the stem, and, when fully deployed to promote hemostasis, a total length of the bandage and the stem being less than the distance from the percutaneous opening to the vascular puncture.

21. The method of claim 20, wherein the stem includes a lumen and is substantially cylindrical.

22. The method of claim 21, wherein the bandage surrounds at least a portion of the stem.

23. The method of claim 17, wherein the bandage includes at least one coagulating material.

24. The method of claim 17, wherein removing the bandage includes removing the bandage from the access tract after achieving hemostasis.

25. The method of claim 17, further including securing the apparatus to prevent the bandage from moving within the access tract.

26. A method of performing a medical operation, comprising:
   creating an opening in an epidermis of a patient;
   forming an access tract in a subcutaneous tissue layer via the opening;
   forming a vascular puncture at an end of the access tract, the vascular puncture extending through a wall of a vessel;
   advancing a stem of an apparatus into the access tract, the apparatus including a bandage fixedly coupled on a distal end of the stem, wherein a total length of the bandage and the stem, when the bandage is fully deployed in the access tract to promote hemostasis, is less than the distance from the opening to the vascular puncture; and
   removing the stem and the bandage through the access tract with the stem fixedly coupled to the bandage.

27. The method of claim 26, wherein removing the stem and the bandage includes removing the stem and the bandage from the access tract after achieving hemostasis.

28. The method of claim 26, further including securing the apparatus to prevent the bandage from moving within the access tract.

29. The method of claim 26, further including:
   prior to advancing the stem, placing a guide wire through the access tract and the vascular puncture and into the vessel;
   threading the apparatus onto the guide wire; and after the bandage has been advanced into the access tract but before removing the stem and the bandage through the access tract, removing the guide wire such that a portion of the access tract collapses.

30. The method of claim 26, further including applying pressure to the apparatus while maintaining the bandage in the access tract.

31. The method of claim 26, wherein the bandage includes a tapered tip and a lumen configured to receive the guide wire.

32. The method of claim 26, wherein the stem is substantially cylindrical and includes a lumen.

33. The method of claim 26, wherein the bandage surrounds at least a portion of the stem.

34. The method of claim 26, wherein the bandage includes at least one coagulating material.

35. A method of performing a medical operation, comprising:
    forming an access tract in a subcutaneous layer of skin via an opening in the skin;
    forming a vascular puncture through a wall of a vessel, the vascular puncture being located at a terminal end of the access tract;
    advancing an apparatus, the apparatus including a delivery mechanism and a bandage fixedly coupled to the delivery mechanism, into the access tract but not into contact with the wall of the vessel or into the vascular puncture, the apparatus promoting hemostasis without contacting the wall of the vessel; and
    after hemostasis occurs, removing the apparatus including the bandage back through the access tract.

36. The method of claim 35, further including securing the bandage to prevent the bandage from moving within the access tract.

37. The method of claim 35, wherein the delivery mechanism further includes a stem, the bandage being located on a distal end of the stem, and, when fully deployed in the access tract to promote hemostasis, a total length of the bandage and the stem being less than the distance from the opening to the vascular puncture.

38. The method of claim 37, wherein the stem includes a lumen and is substantially cylindrical.

39. The method of claim 37, wherein the bandage surrounds at least a portion of the stem.

40. The method of claim 35, further including:
    prior to advancing the apparatus, placing a guide wire through the access tract and the vascular puncture and into the vessel;
    threading the apparatus onto the guide wire; and
    after the bandage has been advanced into the access tract but before removing the apparatus through the access tract, removing the guide wire such that a portion of the access tract collapses.

41. The method of claim 35, further including applying pressure to the apparatus while maintaining the bandage in the access tract.

42. The method of claim 35, wherein the bandage includes a tapered tip and a lumen configured to receive the guide wire.

43. The method of claim 35, wherein the bandage includes at least one coagulating material.

44. A method of operating a hemostatic device comprising a bandage and a delivery mechanism coupled to the bandage, the method comprising:
    directing the delivery mechanism toward a puncture tract to insert the bandage into the puncture tract;
    maintaining a surface of the delivery mechanism outside the puncture tract;
    creating pressure between the bandage and the puncture tract to promote hemostasis when at least a portion of the puncture tract distal to the bandage is collapsed; and
    without disconnecting the delivery mechanism from the bandage, after a period of time, pulling the delivery mechanism away from the puncture tract in order to remove the bandage from the puncture tract.

45. The method of claim 44, wherein pulling the delivery mechanism away from the puncture tract includes pulling the delivery mechanism away from the puncture tract after achieving hemostasis.

46. The method of claim 44, further including securing the delivery mechanism to prevent the bandage from moving within the puncture tract.

47. The method of claim 44, wherein the delivery mechanism further includes a stem, the bandage being located on a distal end of the stem, and, when fully deployed, a total length of the bandage and the stem being less than a length of the puncture tract.

48. The method of claim 44, further including:
    prior to directing the delivery mechanism toward the puncture tract, placing a guide wire through the puncture tract and a vascular puncture;
    threading the delivery mechanism onto the guide wire; and
    after the bandage has been inserted into the puncture tract but before removing the bandage from the puncture tract, removing the guide wire such that the portion of the puncture tract collapses.

49. The method of claim 44, further including applying pressure to the delivery mechanism while maintaining the bandage in the puncture tract.

50. The method of claim 44, wherein the bandage includes:
    a tapered tip on a distal end of the bandage;
    a central lumen; and
    at least one coagulating material.

51. The method of claim 50, wherein creating pressure includes creating pressure between the tip and the portion of the puncture tract.

52. The method of claim 44, wherein the directing step includes inserting the bandage into the puncture tract but not through a vascular puncture.

* * * * *